United States Patent [19]

Cornell

[11] Patent Number: 4,929,577

[45] Date of Patent: May 29, 1990

[54] TRANSPARENT WOUND DRESSINGS IN SHEET FORM

[75] Inventor: John Cornell, West Chester, Pa.

[73] Assignee: Medi-Tech International Corporation, Brooklyn, N.Y.

[21] Appl. No.: 24,265

[22] Filed: Mar. 11, 1987

[51] Int. Cl.$^5$ .............................................. A61L 15/00
[52] U.S. Cl. ...................... 514/58; 514/777; 514/778; 424/443; 424/445; 424/447; 128/156; 523/111; 536/103; 524/48
[58] Field of Search .............. 514/58, 777, 778; 424/443, 445, 447; 128/156; 523/111; 536/103; 524/48

[56] References Cited

U.S. PATENT DOCUMENTS

| | | | |
|---|---|---|---|
| 2,808,381 | 10/1957 | Stone | 524/48 |
| 2,976,178 | 3/1961 | Pahl et al. | 524/48 |
| 3,365,320 | 1/1968 | Minelli | 524/48 |
| 3,425,972 | 2/1969 | Nobile et al. | 524/48 |
| 3,597,374 | 8/1971 | Nagan | 524/48 |
| 3,849,238 | 11/1974 | Gould et al. | 128/156 |
| 4,074,039 | 2/1978 | Lim et al. | 128/156 |
| 4,105,824 | 8/1978 | Monte | 524/48 |
| 4,248,685 | 2/1981 | Beede et al. | 204/159.22 |
| 4,511,646 | 4/1985 | Fohrenkamm et al. | 430/283 |
| 4,554,317 | 11/1985 | Behar et al. | 525/28 |
| 4,556,056 | 12/1985 | Fischer et al. | 128/156 |
| 4,671,267 | 6/1987 | Stout | 128/156 |

OTHER PUBLICATIONS

Geliperm Trade Literature.

*Primary Examiner*—Ronald W. Griffin
*Attorney, Agent, or Firm*—Bernard Malina

[57] ABSTRACT

A transparent gel composition is provided for dressing of skin wounds. The dressing is in the form of a sheet comprising dextrin and a water-swellable, cross-linked polymer selected from polyacrylamide or polymethacrylamide. The ratio of dextrin to polymer ranges from about 2:1 to 1:1.

9 Claims, No Drawings

TRANSPARENT WOUND DRESSINGS IN SHEET FORM

FIELD OF THE INVENTION

The invention concerns novel skin dressings which aid in the healing of wounds.

BACKGROUND OF THE INVENTION

Burns, ulcerations, severe abrasions, skin transplants and similar poorly healing wounds affecting relatively large areas of skin are particularly vulnerable to infection. Artificial skins have been developed as bandages to temporarily protectively cover these wounds. These bandages must promote biofixation, control bacterial growth, supply moisture and prevent evaporation.

U.S. Pat. No. 3,849,238 (Gould et al.) discloses artificial skin comprising a water-containing hydrophilic polymer sponge layer and a thinner hydrophobic polymer layer. Illustrative of the hydrophilic polymers are hydroxyalkyl acrylates or methacrylates, acrylamides, and derivatives thereof. The hydrophobic component may be alkoxyalkyl acrylates or methacrylates, vinylacetate polymers, elastomeric silicone or polymerized olefins such as polyisoprene, polybutadiene or polyethylene.

U.S. Pat. No. 4,248,685 (Beede et al.) reports aqueous hydrocolloidal dispersions of random interpolymers having bacteriostatic properties. These interpolymers can initially be prepared as gels. Gelled material can then be cast into a self-supporting, transparent, conformable film wound dressing. The interpolymers are derived from the polymerization of a monomer mixture comprising 10–90% alpha, beta-olefinically unsaturated carboxylic acid esters with 90–10% alpha, beta-olefinically unsaturated amides capable of being dispersed in water. A difunctional monomer such as $N,N^1$-methylene bisacrylamide must also be present to cross-link the polymer mixture.

U.S. Pat. No. 4,554,317 (Behar et al.) describes a synthetic hydrophilic membrane for use as a wound covering. The membrane is prepared by graft polymerization of a hydrophilic monomer with a polyurethane substrate. Included among the hydrophilic monomers are acrylamides, hydroxyalkyl acrylates and hydroxyalkyl methacrylates. Gamma radiation and x-rays are suggested as suitable for initiating the graft polymerization.

Wound dressings described in the foregoing art are frequently opaque. Visual observation of the healing process is therethrough prevented. Infection or other complications cannot be detected with opaque coverings. Transparent wound dressings would therefore be highly desirable.

Transparent wound dressings are known. A particularly useful form is the gel type which can be cast as a sheet or strip. This type is commercially available, for instance, from Geistlich-Pharma Inc., Atlanta, Ga., under the trademark of GELIPERM. Sheets or strips have the advantage of easy usage, removability without disturbing healing, and promoting improved healing without excess granuloma formation. Most of the aforecited patents disclose compositions unsuitable for casting.

U.S. Pat. No. 4,556,056 (Fischer et al.) discloses transparent gels in sheet or strip form for use as fluid bandages. These sheets are produced by dissolving a monomer and a gellable polysaccharide in water and therein initiating free-radical polymerization of the monomer. While the compositions of this patent substantially improve over the cited art, problems do remain. In particular, the sheets of Fischer et al. as embodied in the GELIPERM product have clinically exhibited too rapid an uptake of moisture Moreover, the preferred polysaccharides described therein tend to gel too severely on wetting causing greater difficulty in handling the components as they are cast into sheets. Control of sheet quality and rate of production also thereby suffer.

Consequently, it is an object of this invention to provide a dressing which is sufficiently transparent to view a wound.

Another object of this invention is to provide a dressing of the sheet or strip variety.

A further object of this invention is the formulation of a dressing that is easily handlable for casting.

A final object of this invention is production of a sheet dressing exhibiting improved control over water absorption.

SUMMARY OF THE INVENTION

A transparent aqueous gel composition is provided for dressing skin wounds in the form of a sheet comprising:

(i) a dextrin; and
(ii) a water-swellable cross-linked polymer selected from polyacrylamide or polymethacrylamide, wherein the ratio of dextrin to polymer ranges from about 2:1 to 1:1.

DETAILED DESCRIPTION OF THE INVENTION

It has been discovered that the saccharide dextrin is unexpectedly effective as a controlled swelling agent for wound dressings when combined with certain polymers. Dextrin is a non-cross-linked carbohydrate intermediate between starch and the sugars. The material is produced from starch through hydrolysis by dilute acids, distase or dry heat. Other common names for dextrin are British gum, starch gum, amylin and gummeline; the general structure is $(C_6H_{10}O_5)_x$ wherein x may be a value from 6 to 7. The saccharide may be obtained commercially from the American Maize-Products Company, a preferred grade being known as Dextrin 1104.

Unlike gelling agents such as agar-agar, dextrin does not gel when wetted. Immediate gelling is undesirable. Delayed gellation permits sufficient time for liquid absorption by the entire composition and aids the swelling agent to produce controlled fluid sorption by the polymer. Thus, there is greater tolerance in preparation of the dressing. Lumping during fluid absorption is thereby avoided. A beneficial aspect of dextrin containing wound dressings as herein described, is the superior water absorption profile (i.e. controlled wetting). Similarly formulated gels employing sorbitol or gelatin were found to have much slower rates of moisture absorption than the dextrin compositions. Mono and disaccharides have little structure in the fluid swollen gel, while starch or cellulosics do not aid in fluid absorption control.

A second important component of the dressing of this invention is the hydrophilic polymer. Cross-linked, water-swellable polyacrylamides or polymethacrylamides have been determined to be the most suitable hydrophilic polymers. Generally, these polymers may be obtained by free-radical polymerization of acrylamide (or methacrylamide) using an appropriate radical initiator catalyst. Appropriate catalysts include sodium monopersulfate, sodium percarbonate, and other water soluble hydrogen peroxide generators. Under certain circumstances there may alternatively be employed organic nitrogen type radical initiators such as azobisisobutyronitrile. Gamma radiation and x-rays may also be utilized to initiate polymerization in a water phase; irradiation will then further induce cross-linking.

Peroxides or nitrogen type initiators themselves may require a promotor or activator to begin generation of free-radicals at ambient conditions. Amines are highly effective promotors of peroxide decomposition. A preferred amine for use with persulfate is tetramethylethylene diamine. Initiation or promotion of nitrogen type initiators is best done with heat or ultraviolet radiation.

Besides the acrylamide or methacrylamide monomer, there must also be present a cross-linking agent. Particularly preferred for cross-linking is methylenebisacrylamide. Of course, other difunctional monomers may also be useful including divinylbenzene or ethylenedimethacrylate.

Another important, in fact critical, parameter in forming the dressing is the relative amount of swelling agent to polymer. The swelling agent to polymer ratio must lie between 2:1 to 1:1. Preferably, the ratio ranges between 2:1 and greater than 1:1, ideally about 1.5:1 to 1.1:1.

In concentration terms, the weight of cross-linked polyacrylamide or polymethacrylamide will comprise from about 1% to 20% by weight of the final dressing. Preferably, the polymer concentration will range from about 5% to 15%, optimally about 10%. Dextrin will similarly be present from about 1% to 20% by weight of the final dressing; preferably 5% to 15%, optimally about 10%.

Other components of the composition include water found in amounts from about 50% to 90%; preferably, from 65% to 80%.

The following examples will more fully illustrate various embodiments of the present invention, all parts and percentages therein being by weight, unless otherwise noted.

EXAMPLE 1

A typical formulation is outlined in the table below.

TABLE I

| | Formulation | | |
|---|---|---|---|
| | Components | Weight (grams) | Percent |
| Part I: | Acrylamide | 400 | 10 |
| | Dextrin 1104 | 400 | 10 |
| | Methylenebisacrylamide | 0.35 | 0.08 |
| | Tetramethylethylene diamine | 0.4 | 0.1 |
| | Distilled Water | 3,000 | 75 |
| Part II: | Distilled Water | 180 | 5 |
| | Sodium Persulfate | 20 | 0.05 |
| | Total | 4,000 | |

Distilled water, in an amount listed in Part I, is heated to 60° C. Dextrin is slowly added thereinto with mixing until there is complete dissolution. Thereafter, the remaining components including acrylamide, methylenebisacrylamide, and tetramethylenediamine. Part I is stable for several days at room temperature. Part II is an aqueous solution of the free-radical initiator, sodium persulfate; this solution is stable for at least several weeks.

When ready to fill trays, Part I is mixed with Part II at 60° C. The preferred blending method is to fill the trays directly from a motionless mixer. These trays are similar to commercial polyethylene meat trays. Prior to being filled, each tray is coated with a release agent. Silicone or Pam may be used as the release agent.

Each tray is filled with about 100–150 grams and allowed to cure. Curing occurs rapidly (within 3–15 minutes). Post cure, when desired for removal of residual acrylamide monomer, is usually performed by placing the trays in an oven for 3 hours at 60° C.

EXAMPLE 2

The following example illustrates the effect of other swelling agents on water absorption when combined with polyacrylamide. Sheets were cast in a process similar to that described in Example 1. The compositions are outlined in Table II. Water absorption values may be found in Table III.

TABLE II

| | Acrylamide-Swelling Agent Compositions | | | |
|---|---|---|---|---|
| | | Composition Number (Weight-Grams) | | |
| | Components | 1 | 2 | 3 |
| Part I: | Acrylamide | 100 | 100 | 100 |
| | Methylenebisacrylamide | 0.17 | 0.17 | 0.17 |
| | Tetramethylethylene diamine | 0.1 | 0.1 | 0.1 |
| | Distilled Water | 750 | 750 | 750 |
| | Dextrin 1104 | 100 | — | — |
| | Sorbitol | — | 100 | — |
| | Gelatin | — | — | 100 |
| Part II: | Distilled Water | 45 | 45 | 45 |
| | Ammonium Persulfate | 5 | 5 | 5 |

TABLE III

| | Water Absorption Rates | | |
|---|---|---|---|
| Composition No. | Swelling Agent | Water Absorption (%) | Time (min.) |
| 1 | Dextrin | 65 | 2 |
| | | 100 | 3.5 |
| | | 109 | 5 |
| | | 120 | 10 |
| 2 | Sorbitol | 40 | 10 |
| | | 60 | 20 |
| | | 80 | 30 |
| | | 90 | 40 |
| | | 120 | 120 |
| 3 | Gelatin | 13 | 10 |
| | | 19 | 20 |
| | | 20 | 40 |

From Table III it is evident that gelatin-polyacrylamide sheets have a very low, and inadequate, rate of water absorption. Only 20% water was taken up after a full 40 minutes. Sorbitol-polyacrylamide sheets exhibited better, but still inadequate, water absorption properties. After 40 minutes, absorption reached 90%. By contrast, the dextrin-polyacrylamide compositions had a water absorption of 100% after 3.5 minutes.

Various modifications and changes may be made with regard to the foregoing detailed description without departing from the spirit and scope of this invention.

What is claimed is:

1. A transparent gel composition for dressing skin wounds in the form of a sheet comprising:
    (i) a dextrin; and
    (ii) a water-swellable, cross-linked polymer selected from polyacrylamide or polymethacrylamide, wherein the ratio of dextrin to polymer is from about 2:1 to 1:1.

2. A composition according to claim 1 wherein the ratio of dextrin to polymer ranges between 2:1 and greater than 1:1.

3. A composition according to claim 1 wherein the ratio of dextrin to polymer ranges between 1.5:1 to 1.1:1.

4. A composition according to claim 1 wherein the polymer is polyacrylamide.

5. A composition according to claim 1 wherein the polymer is polymethacrylamide.

6. A composition according to claim 1 having water present in an amount from about 50% to 90% by weight.

7. A composition according to claim 1 having water present in an amount from about 65% to about 80%.

8. A method for healing wounds comprising applying a transparent gel composition as a dressing over a skin wound, said composition being in the form of a sheet comprising:
 (i) a dextrin; and
 (ii) a water-swellable, cross-linked polymer selected from polyacrylamide or polymethacrylamide,
wherein the ratio of dextrin to polymer is from about 2:1 to 1:1.

9. A method according to claim 8 wherein said composition includes water present in an amount from about 50% to about 90% by weight.

* * * * *